United States Patent [19]
Bisgard-Frantzen et al.

[11] Patent Number: 6,106,828
[45] Date of Patent: Aug. 22, 2000

[54] CONJUGATION OF POLYPEPTIDES

[75] Inventors: Henrik Bisgard-Frantzen, Bagsvaerd; Arne Agerlin Olsen, Virum; Annette Prento, Ballerup, all of Denmark

[73] Assignee: Novo Nordisk A/S, Bagsvaerd, Denmark

[21] Appl. No.: 09/123,787

[22] Filed: Jul. 28, 1998

Related U.S. Application Data

[63] Continuation of application No. PCT/DK97/00051, Feb. 7, 1997.

[30] Foreign Application Priority Data

Feb. 15, 1996 [DK] Denmark ................................. 0154/96

[51] Int. Cl.$^7$ .......................... A61K 38/43; A61K 38/00; C12N 11/00; C12N 11/06; A01N 37/18
[52] U.S. Cl. ........................ 424/94.1; 424/94.2; 435/174; 435/175; 435/176; 435/177; 435/178; 435/179; 435/180; 435/181; 514/2; 514/8; 514/12; 530/322; 530/323
[58] Field of Search ..................................... 435/174, 175, 435/176, 177, 178, 179, 180, 181; 530/350, 322, 323; 424/94.1, 94.2; 514/2, 8, 12

[56] References Cited

U.S. PATENT DOCUMENTS

| | | | |
|---|---|---|---|
| 4,179,337 | 12/1979 | Davis et al. ............................. | 435/181 |
| 4,935,465 | 6/1990 | Garman .................................. | 525/54.1 |
| 5,006,333 | 4/1991 | Saifer et al. ............................... | 424/78 |
| 5,133,968 | 7/1992 | Nakayama et al. ..................... | 424/401 |
| 5,230,891 | 7/1993 | Nakayama et al. ..................... | 424/401 |
| 5,283,317 | 2/1994 | Saifer et al. ............................ | 528/405 |
| 5,298,643 | 3/1994 | Greenwald ................................ | 558/6 |
| 5,321,095 | 6/1994 | Greenwald ............................. | 525/404 |
| 5,349,001 | 9/1994 | Greenwald et al. .................... | 525/408 |
| 5,637,749 | 6/1997 | Greenwald ................................ | 558/6 |
| 5,698,405 | 12/1997 | Goldenberg .............................. | 435/7.5 |
| 5,856,451 | 1/1999 | Olsen et al. ............................ | 530/402 |
| 5,955,079 | 9/1999 | Mond et al. .......................... | 424/193.1 |
| 5,989,899 | 11/1999 | Bower et al. ............................ | 435/263 |

FOREIGN PATENT DOCUMENTS

| | | |
|---|---|---|
| 0 183 503 | 6/1986 | European Pat. Off. . |
| 0 233 221 | 5/1987 | European Pat. Off. . |
| WO 96/17929 | 6/1996 | WIPO . |
| WO 96/40791 | 12/1996 | WIPO . |

*Primary Examiner*—Einar Stole
*Attorney, Agent, or Firm*—Steve T. Zelson, Esq.; Reza Green, Esq.

[57] ABSTRACT

The present invention provides polypeptide conjugates with reduced allergenicity comprising a polymeric carrier molecule having two or more polypeptide molecules coupled thereto. The invention also provides methods for producing the conjugates, compositions comprising the conjugates, and the use of the conjugates in industrial applications, including personal care products and detergent compositions.

40 Claims, 3 Drawing Sheets

CONJUGATION OF POLYPEPTIDES

CROSS-REFERENCE TO RELATED APPLICATIONS

This application is a Continuation application of PCT/DK97/00051 filed on Feb. 7, 1997 and claims priority under 35 U.S.C. 119 of Danish application 0154/96 filed on Feb. 15, 1996, the contents of which are fully incorporated herein by reference.

FIELD OF THE INVENTION

The present invention relates to a polypeptide conjugate with reduced allergenicity, a process for producing said polypeptide conjugate with reduced allergenicity, compositions comprising said polypeptide conjugate with reduced allergenicity, the use of said polypeptide conjugate for reducing the allerginicity of a vast number of industrial products and the use in a number of applications, such as the use in personal care products and in detergent compositions.

BACKGROUND OF THE INVENTION

An increasing number of polypeptides, including proteins and enzymes, such as proteases, are being produced industrially by microorganisms for use in industry, household, food/feed, cosmetics or medicine etc. Said polypeptides may under certain circumstances inflict a potential risk to especially employees handling the manufacturing of products containing polypeptides, and also to some extent to users of these products, such as hairdressers, and end-users of cosmetic and toiletry products etc.

This potential risk need to be controlled and/or limited.

Allergenicity of polypeptides

In general polypeptides are potential antigens toward which the human immune system can produce specific antibodies upon exposure. This process is known as "immunization" when a clinical beneficial response is obtained whereas the term "sensitization" is applied when the response leads to hypersensitivity. During the primary exposure clonal selection and expansion of the specific B-cell clones are initiated, meaning that a protective or allergic response will only be a clinically manifest upon following exposures. The allergic reaction can be defined as an pathological immune response elicited by otherwise unharmful agents in low concentrations. The process of sensitisation leading to type I hypersensitivity are characterized by the formation of specific IgE antibodies. At present, the mechanism controlling the subclass shifting are not fully understood.

IgE secreted from activated B-cells can attach to Fcε receptors located on the surface of mast cells and basophil granulocytes, which contain numerous cytoplasmic granules packed with chemical mediators e.g. histamine (J. Klein, "Immunology", Blackwell Sci. Pub., London, 1990; E. Benjamini & S. Leskowitz, "Immunology", Wiley-Liss, N.Y. 1991).

In atopic individuals each of these cells can have a high number of IgE molecules bound to its surface, where they can remain available to interact with allergens for weeks. Upon contact with an allergen the surface bound IgE cross-binds the allergen, leading to the release of cytoplasmic granules into the proximity of the cell, thereby causing the inflammatoric allergic reaction.

The role of IgE has been shown to relate to natural immunologic defence systems towards parasitic worms infections and the development of allergies has been suggested to be an unfortunate by-product of this defence system.

The natural allergens causing IgE mediated hypersensitivity can be classified according to their way of exposure: Inhalant allergens (pollens, dust mites etc.), Ingested allergens (milk, eggs etc.); contact allergens (e.g. from latex) and allergens from stinging insects (e.g. bees, fire ants etc.). The aero-allergens represents clinically by far the largest group, stressing an area of high potential risk for the industrial polypeptides.

Testing for allergy can either be performed as in vivo provocation, most commonly skin prick testing of by a number of in vitro assays, primarily based on IgE levels in pheriperal blood. In spite of the great efforts in the latter area the most reliable way to diagnose allergy is still the in vivo challenging, which again has different levels of sensitivity depending on the selected target organ.

For instance, intranasal challenge with allergenic proteins can provoke an allergic response even though skin tests and radio-allergosorbent test (RAST) for specific serum IgE are negative (Ivan Roitt, "Essential Immunology", fifth edition, p. 152 and p. 240, 1984).

Reduction of allergenicity of Polypeptides

Presently, the generation of allergic responses to industrial polypeptides is avoided by immobilizing, granulating, coating or dissolving the products, especially to avoid the formation of airborne material. Anyhow, these methods still represent a risk of dust or aerosol formation during handling and processing, with the subsequent risk of allergic sensitisation.

There will, anyhow, still be a risk of having polypeptide dust or dissolved polypeptide in aerosol form. Therefore some release of enzymes can occur leading to a possible sensitisation and subsequent allergic response.

Another way of diminishing the problem has been to select polypeptides of human origin for production, e.g. in bacteria, fungi, yeast, or mammalian cell cultures. Furthermore, it will in many cases not be possible to find polypeptides of human origin with the desired properties, wherefore other origin has to be considered. This can be either human polypeptides that are altered in one or more positions in the molecule, giving the performance that is desired. It might also be molecules from other species, including bacteria, mold etc. All the latter groups of products will have potency for immune stimulation in mammalians.

A further proposition for decreasing allergenicity has been to reduce the size of the protein molecules (see e.g. JP Patent Publication No. 4,112,753, or Research Disclosure No. 335,102). This is, however, a solution that is only available when the activity of the protein is without importance, or in such rare cases, where the activity of the protein is retained in spite of a breakdown of the protein.

The application of protein engineering has been suggested to reduce the allergenicity of proteins through epitope mapping and subsequent change of the allergenic epitopes (see WO 92/10755 (Novo Nordisk A/S). This procedure usually requires a large investment in work and development.

Another technology which can be used for reducing the immune system's response towards polypeptides is the "PEGylation"-technology, which involves modification of polypeptides by means of covalent attachment of strands of polyethylene glycol (PEG), to polypeptide molecules. This technique have been known for more than 20 years (see e.g. U.S. Pat. No. 4,179,337), but is today only used in connection with polypeptides for pharmaceutical use. Consequently the main purpose is to reduce the immune system's production of IgM and/or IgG.

µg Dextran-Peroxidase A and B intratracheally found to be enzyme specific positive vs. weeks starting from the day of exposure.

Figure 2:
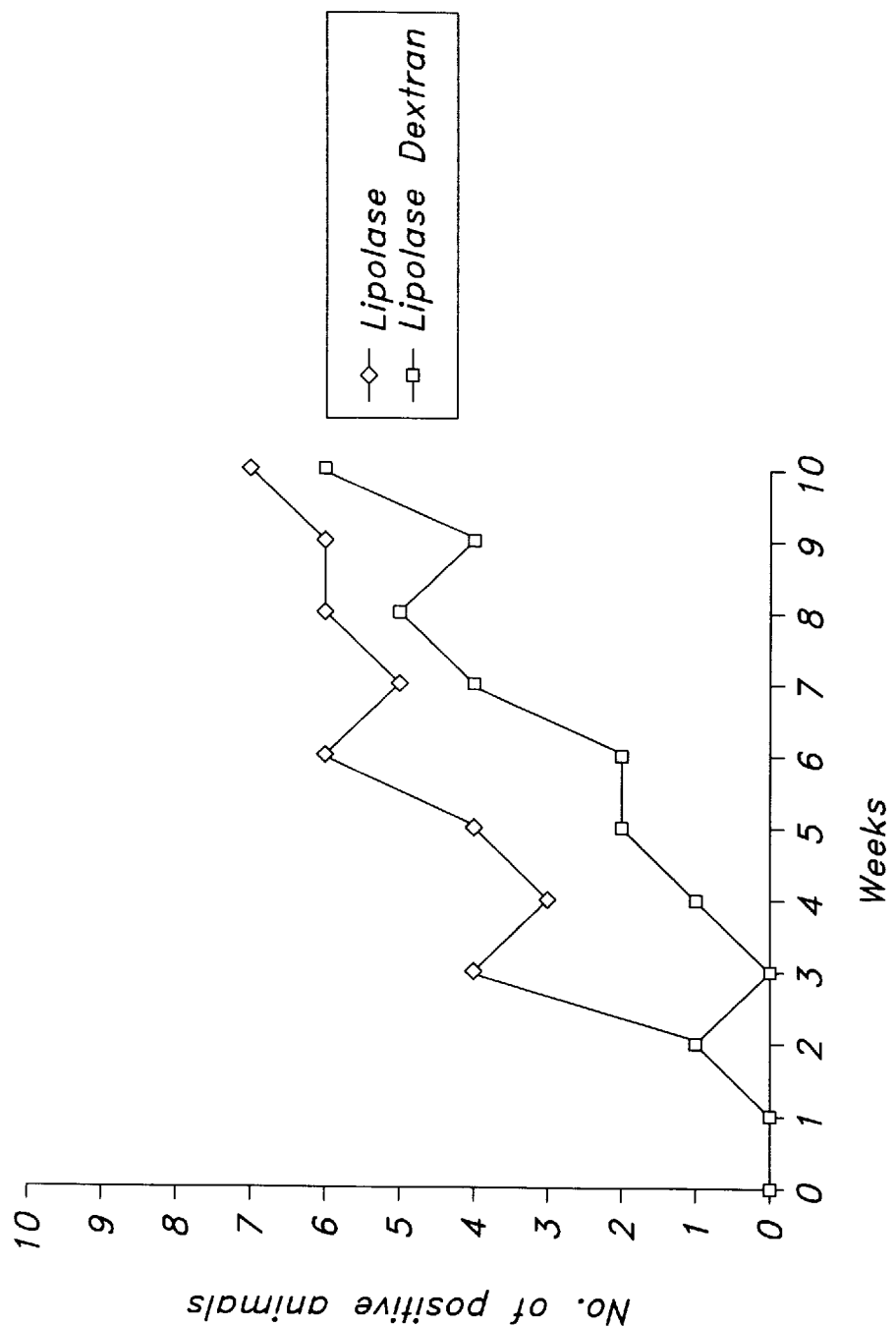

FIG. 2 shows the number of Dunkin Hartley guinea pig having been exposed to 1.0 µg lipase and 1.0 µg Dextran-lipase intratracheally found to be enzyme specific positive vs. weeks starting from the day of exposure.

Figure 3:
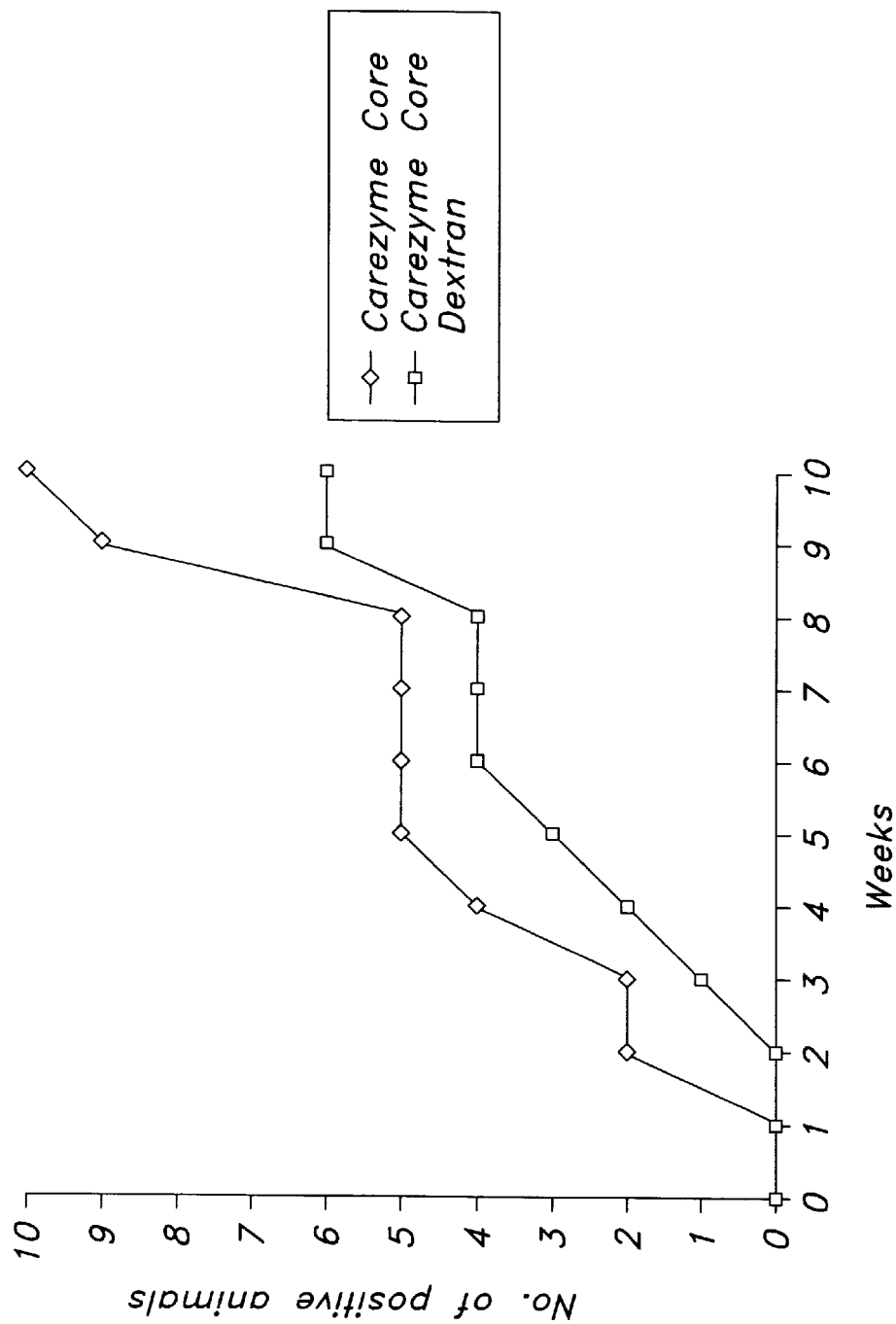

FIG. 3 shows the number of Dunkin Hartley guinea pig having been exposed to 1.0 µg cellulase and 1.0 µg Dextran-cellulase intratracheally found to be enzyme specific positive vs. weeks starting from the day of exposure.

SUMMARY OF THE INVENTION

It is the object of the present invention to provide polypeptide conjugates with reduced allergenicity.

It is to be understood that, in connection with industrial applications of polypeptides, it is mainly the inhalation of the allergens that may inflict a risk of an allergic response. Therefore, one of the crucial advantages of the present invention is that the inventors have solved the problem of the respiratory challenge with allergens, whereas prior art solutions mainly concern dermal challenge with alleged immunogens. The respiratory challenge is a much more sensitive question.

A few important terms essential for the understanding of the present invention will be defined in the following, as these terms are often used in connection with the description the immune systems response towards polypeptides, in a unclear manner, even by many scientists.

Immunogenicity, antigenicity and allergenicity

"Immunogenicity" is a wider term than "antigenicity" and "allergenicity" and expresses the immune systems response to the presence of foreign substances. Said foreign substances are called "immunogens", "antigens" and "allergens", respectively, depending on the type of immune response they elicit.

An "immunogen" is a substance which, when introduced into circulatory system of animals and humans, is capable of stimulating an immunologic response.

The term "antigen" refers to substances which by themselves are capable of generating antibodies when recognized as a non-self molecule.

An "allergen" is an antigen which gives rise to allergic sensitization or an allergic response due to the formation of IgE antibodies (in humans, and molecules with comparable effects in animals).

The above used term "circulatory system" of the body of humans and animals means in the context of the present invention the system which mainly consist of the heart and blood vessels. The heart delivers the necessary energy for maintaining blood circulation in the vascular system. The circulation system functions as the organisms transportation system, transporting (in the blood) $O_2$, nutritious matter, hormones, and other substances of importance for the cell regulation into the tissue. Further, the blood removes $CO_2$ from the tissue to the lungs and residual substances to e.g. the kidneys. Furthermore, the blood is of importance for the temperature regulation and the defence mechanisms of the body, including the immune system.

In the context of the present invention a polypeptide conjugate having "reduced allergenicity" indicates that the amount of produced IgE (in humans, and molecules with comparable effects in specific animals), which might lead to an allergic state, is significantly decreased when inhaling a polypeptide conjugate of the invention in comparison to the corresponding parent polypeptide molecule.

As mentioned above it is, at least in the context of polypeptides of the present invention, important to distinguish between dermal allergens mediating allergic responses caused by skin contact, and respiratory allergens causing allergic responses by contact with cell-bound IgE in the bronchial tree, due to the well-known fact that skin tests may be negative even though inhalation tests provoke an allergic response.

Therefore, assessment of allergenicity may be made by inhalation tests, comparing the effect of intratracheal administrated parent polypeptides with the corresponding polypeptides of the invention with reduced allergenicity.

A number of in vitro animal models exist for assessment of the allergenicity of polypeptides. Some of these models give a suitable basis for hazard assessment in man. Suitable models include a guinea pig model and a rat model. These models seek to identify respiratory allergens as a function of elicitation reactions induced in previously sensitised animals. According to these models the alleged allergens are introduced intratracheally into the animals.

A suitable strain of guinea pigs, the Dunkin Hartley strain, does not as humans, produce IgE antibodies as the allergic response. However, they produce another type of antibody the IgGlA and IgGlB (see e.g. Prentø, ATLA, 19, p. 8–14, 1991), which are responsible for their allergenic response to inhaled polypeptides including enzymes. Therefore, when using the Dunkin Hartley animal model, the relative amount of IgG1A and IgG1B is a measure of the allergenicity level.

A rat strain suitable for intratracheal exposure to polypeptides and enzymes is the Brown Norway strain. The Brown Norway strain produces IgE as the allergic response.

Other animals such as rabbits etc. may also be used for comparable studies.

In Example 1 the surprising discovery of the present invention is disclosed showing that the allergenicity of purified wild-type *Coprinus cinerea* peroxidase coupled to dextran ($M_r$ about 1,000 kDa) intratrachaelly introduced into Dunkin Hartley guinea pigs is reduced in comparison to the corresponding monomer peroxidase ($M_r$ about 39 kDa).

Example 2 and 3 show that also the allergenicity of lipase and cellulase, respectively is reduced.

In the first aspect the invention relates to a polypeptide conjugate with reduced allergenicity which comprises one polymeric carrier molecule having two or more polypeptide molecules coupled covalently thereto.

The polypeptide molecules may be coupled to the polymeric carrier molecule using any methods. It is well-known by a person skilled in the art to couple chemical groups on the polypeptides, such as free hydrolxy groups, free sulfhydryl groups, free acid groups, free amino groups, to hydroxy groups of a vast number of polymeric (carrier) molecule.

In an embodiment of the invention the polymeric carrier molecule is coupled with two or more polypeptide molecules via a covalent linkage formed between one of the two vinyl groups of a divinyl sulfone.

The term "polypeptides" means in the context of the present invention all types of polypeptides such as proteins, enzymes, ligands, antibodies, inhibitors, receptors which may constitute a greater or less part of a commercial product. Especially contemplated are polypeptides which, as ingredients in a commercial product, are not to be introduced into the circulatory system of the body of humans or animals.

In the second aspect the invention relates to a process for producing polypeptides with reduced allergenicity comprising the steps of i) activating a polymeric carrier molecule, and
ii) reacting two or more polypeptide molecules with said activated polymeric carrier molecule under conditions suitable for conjugation, and
iii) blocking of residual active groups on the conjugate.

In a preferred embodiment of the process of the invention the polymeric carrier molecule is coupled directly with two or more polypeptide molecules or via a reactive linker molecule.

The activation of the polymeric carrier molecule in step i) may be performed by any method known in the art. Examples of such suitable coupling methods will be described below.

In an embodiment of the invention two or more polypeptide molecules are coupled to the polymeric carrier molecule via a divinyl sulfone.

The third object of the invention is to provide compositions comprising a polypeptide conjugate of the invention.

Such compositions may further comprise polypeptides, such as proteins and/or enzymes and/or ingredients normally used in e.g. products such as detergents, household article products, agrochemicals, personal care products, cosmetics, toiletries, oral-, skin and hair care products, composition use for processing textiles, compositions for cleaning hard surfaces, compositions used for manufacturing food, feed, juice, wine and beverages, and also oral and dermal pharmaceuticals.

The above group of products is sometimes referred to as "industrial products". This term will be used below to describe the group of products which are especially contemplated according to the present invention.

In the final aspect the invention relates to the use of polypeptide conjugates of the invention for a number of applications for industrial products, such as personal care applications and the use in detergent compositions.

DETAILED DESCRIPTION OF THE INVENTION

It is the object of the invention to provide polypeptide conjugates with reduced allergenicity.

As described above it is well-known according to prior art to conjugate one or more polymeric molecules to one polypeptide carrier molecule by covalently attaching one or more of polymeric molecules to e.g. the amino-groups of a polypeptide carrier molecule. Even though techniques for doing so have been shown to reduces the immune system's response towards polypeptides said techniques have some deficiencies:

As the number of accessible attachment-groups (e.g. amino groups) on many polypeptide molecules, used as ingredients in industrial products (i.e. normally polypeptide molecules with a molecular weight in the range from about 10 to 200 kDa), are limited, the number of polymeric molecules which can be conjugated to each polypeptide carrier molecule is limited.

the activity (e.g. catalytic activity) of polypeptide conjugates (e.g. enzyme conjugates) having a number of polymeric molecules attached to each polypeptide carrier molecule is usually significantly decreased in comparison to the corresponding parent polypeptide molecule, due to steric hindrance (i.e. low accessibility of the substrate to the active site of the polypeptide molecule, e.g. enzyme).

The inventors have found that conjugation techniques resulting in the coupling of two or more polypeptide molecule to each polymeric carrier molecule reduces the allergenicity of polypeptide molecules suitable for industrial products.

Such polypeptide conjugates are also more stable than corresponding parent polypeptide molecules.

Polypeptide conjugates according to the present invention may also have advantages in comparison to polypeptide conjugates having several polymeric molecules attached to each polypeptide carrier molecules, as the amount of excess polypeptide molecules needed for the conjugation process is less than the amount needed for corresponding prior art processes conjugating several polymeric molecules to each polypeptide carrier molecule, as only one attachment-group on the polypeptide molecule is needed.

the activity (e.g. catalytic activity) of polypeptide conjugates of the invention is maintained to a greater extent than corresponding prior art polypeptide conjugates having several polymeric molecules attached to each polypeptide carrier molecules, as the steric hindrance is less.

Conjugates of the invention

Accordingly, in the first aspect the invention relates to polypeptide conjugates with reduced allergenicity which comprise one polymeric carrier molecule having two or more polypeptide molecules coupled covalently thereto.

The two or more polypeptide molecules may be coupled to the polymeric carrier molecule by any method known in the art.

In an embodiment of the invention said conjugate comprises a polymeric carrier molecule having coupled thereto, via a covalent linkage, formed between one of the two vinyl groups of a divinyl sulfone, one or more polypeptide molecules.

The total molecular weight ($M_r$) of said polypeptide conjugate lies in the range between 50 kDa and 40,000 kDa, preferably between 100 kDa and 1000, especially 200 kDa and 500 kDa.

Further, conjugates according to the invention have between 1 and 60, preferably 2 and 40, especially 3 and 20 polypeptide molecules coupled to each polymeric carrier molecule.

It is within the scope of the invention to couple two or more different polypeptide molecules to each polymeric carrier molecule. The different polypeptides may exhibit different activities, such as two different enzyme activities. Further, said polypeptide molecules may also be functionally different.

Examples of functionally different polypeptide molecules include enzyme molecules, ligand molecules, inhibitor molecules, receptor molecules and antibody molecules.

Further, it is also possible to provide conjugates having coupled thereto e.g.. an enzyme, such as an oxidase and an effector molecule (i.e. an enhancer). Due to the proximity of said two molecules a very effective conjugate can be obtained.

The Polymeric carrier molecule

The polymeric carrier molecule to which the polypeptide molecules are to be coupled may be any polymer with more than two attachment groups. This includes natural or synthetic homopolymers, such as polyols (i.e. poly-OH), polyamines (i.e. poly-$NH_2$) and polycarboxyl acids (i.e. poly-COOH), and further heteropolymers i.e. polymers comprising at least two different attachment groups e.g. a hydroxyl group and amine groups.

The synthetic homo- and heteropolymeric carrier molecules include Star-polyethylene glycols (PEGs), Branched PEGs, polyvinyl alcohol (PVA), polycarboxylates, polyvinylpyrrolidone and poly-D,L-amino acids.

Star-PEGs are multi-armed polyethylene glycol molecules made by polymerization of ethylene oxide molecules from a crosslinked divinyl benzene core (Gnanou et al. (1988), Makromol. Chem. 198, 2885; Rein et al (1993), Acta Polymer, 44, 225). Star-PEGs and also Branched PEGs are available from Shearwater Inc., USA).

Examples of suitable naturally occurring homo- and heteropolymers comprise dextrans including carboxymethyldextrans, celluloses such as methylcellulose, carboxymethylcellulose, ethylcellulose, hydroxyethylcellulose and hydroxypropylcellulose, hydrolysates of chitosan, starches, such as hydroxyethyl-starches and hydroxypropyl-starches, glycogen, agarose, guar gum, inulin, pullulan, xanthan gum, carrageenin, pectin, alginic acid etc.

In an embodiment of the invention the molecular weight of the polymeric carrier molecule lies between 1 kDa and 10,000 kDa, preferably between 2 kDa and 5,000 kDa, especially between 5 kDa and 500 kDa.

Note that all polymer molecular weights mentioned in connection with the present invention are average molecular weights.

The polypeptide molecule

The polypeptide molecules to be coupled to the polymeric carrier molecule may be any type of polypeptide molecules. However, it is preferred that said polypeptide molecule have some sort of functionality.

The polypeptide to be modified according to the invention may be of plant, animal or microbial origin, although the polypeptide molecules of microbial origin, such as of bacterial or fungal origin (i.e. originated from filamentous fungi or yeasts) are preferred.

Especially contemplated polypeptide molecules are proteins having either an anti-microbial, biological or enzymatic activity.

In the case of the protein being an enzyme it may be an enzyme from the group including hydrolases, such as proteases, lipases and cellulase, transferases, carbohydrases, oxidoreductases, such as laccase and peroxidase, or phytases.

Most enzymes used in industrial products have a molecular weight in the range from about 4 kDa to 200 kDa, preferably 15 kDa to 150 kDa, especially 20 to 100 kDa.

Ligands contemplated according to the invention will in most case have a molecular weight in the range from 100 dalton to 2,000 dalton.

The inventors have found that the enzymatic activity of enzyme conjugates of the invention are substantially maintained.

A "substantially" maintained activity is in the context of the present invention defined as an activity which is at least between 20% and 30%, preferably between 30% and 40%, more preferably between 40% and 60%, better from 60% up to 80%, even better from 80% up to about 100%, in comparison to the activity of the parent unmodified polypeptide molecule.

The process of the invention

In the second aspect the invention relates to a process which is suitable for large scale processing of polypeptide molecules to obtain polypeptide conjugates with reduced allergenicity.

According to the invention one or more polypeptide molecules are coupled to each polymeric carrier molecule by
 i) activating said polymeric carrier molecule, and
 ii) reacting one or more polypeptide molecules with said activated polymeric carrier molecule under conditions suitable for obtaining conjugation, and
 iii) blocking of residual active groups on the conjugate.

The activation of the polymeric carrier molecule in step i) may be performed by any method known in the art. Examples of such methods are described in the following.

Activation of the Polymeric carrier molecule

Methods and chemistry for activation of polymeric molecules as well as for conjugation of polypeptides are intensively described in the literature. Commonly used methods for activation of insoluble polymeric molecules include activation of functional groups with cyanogen bromide, periodate, glutaraldehyde, biepoxides, epichlorohydrin, divinylsulfone, carbodiimide, sulfonyl halides, trichlorotriazine etc. (see R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). Some of the methods concern activation of insoluble polymeric molecules but are also applicable to activation of soluble polymeric molecules e.g. periodate, trichlorotriazine, sulfonylhalides, divinylsulfone, carbodiimide etc. The functional groups being amino, hydroxyl, thiol, carboxyl, aldehyde or sulfydryl on the polymeric molecule and the chosen attachment group(s) on the polypeptide molecule(s) must be considered when choosing the activation and conjugation chemistry.

Techniques involving coupling electrophilically activated polyols to the amino groups of lysins can also be useful. Many of the usual leaving groups for alcohols give rise to an amine linkage. For instance, alkyl sulfonates, such as tresylates (Nilsson et al., (1984), Methods in Enzymology vol. 104, Jacoby, W. B., Ed., Academic Press: Orlando, p. 56–66; Nilsson et al., (1987), Methods in Enzymology vol. 135; Mosbach, K., Ed.; Academic Press: Orlando, p. 65–79; Scouten et al., (1987), Methods in Enzymology vol. 135, Mosbach, K., Ed., Academic Press: Orlando, 1987; p. 79–84; Crossland et al., (1971), J. Amr. Chem. Soc. 1971, 93, p. 4217–4219), mesylates (Harris, (1985), JMS-REV. Macronol. Chem. Phys. C25, 325–373; Harris et al., (1984), J. Polym. Sci. Polym. Chem. Ed. 22, p. 341–352), aryl sulfonates like tosylates, and para-nitrobenzene sulfonates can be used.

Organic sulfonyl chlorides, e.g. Tresyl chloride, effectively converts hydroxy groups in a number of polymeric molecules into good leaving groups (sulfonates) that, when reacted with nucleophiles, like amino groups in the polypeptide chain, allow stable linkages to be formed between the polymeric molecule and the polypeptide molecules. In addition to high conjugation yields, the reaction conditions are in general mild (neutral or slightly alkaline pH, to avoid denaturation and little or no disruption of activity), and satisfy the non-destructive requirements of the polypeptide molecules.

Oxirane groups and other epoxide groups may also been used for creating amine bonds.

Converting a polymeric carrier molecule, such as a polyol, into a chloroformate with phosgene gives rise to carbamate linkages to lysin groups in the polypeptide chain. This theme can be played in many variants substituting the chlorine with N-hydroxy succinimide, imidazole, para-nitrophenol, DMAP. The derivatives are usually made by reacting the chloroformate with the desired leaving group. All these groups give rise to carbamate linkages to the polypeptide.

Furthermore, isocyanates and isothiocyanates may be employed yielding ureas and thioureas, respectively.

Amides may be obtained from polyol acids using the same leaving groups as mentioned above and cyclic imid thrones. Polyol succinate made from reaction with succinic anhydride can also be used.. The hereby comprised ester group make the conjugate much more susceptible to hydrolysis. This group may be activated with N-hydroxy succinimide.

Furthermore, a special linker can be introduced. The oldest being cyanuric chloride (Abuchowski et al., (1977), J. Biol. Chem., 252, 3578–3581; Shafer et al., (1986), J. Polym. Sci. Polym. Chem. Ed., 24, 375–378.

Coupling to the polymeric carrier molecule of aromatic amine followed by diazotation yields a very reactive diazonium salt which in situ can be reacted with polypeptide molecules. An amide linkage may also be obtained by reacting an azlactone derivative of polyols thus introducing an additional amide linkage.

Amino-groups of the polypeptide molecules may also be attached to polyols with carbamate linkages. Lysine residues may be used as the backbone.

In a specific embodiment two or more polypeptide molecules are coupled to each polymeric carrier molecules by a) activating said polymeric carrier molecule by coupling thereto a reactive moiety, and b) reacting two or more polypeptide molecules with said activated polymeric carrier molecule.

In an embodiment of the invention the activation in step a) is performed by covalently linking thereto a reactive moiety derived from divinyl sulfone.

Details on how to conjugate one or more polypeptide molecules to each polymeric carrier molecule using divinyl sulfone as the attachment group is provided in for instance WO 93/01498 from Immunodex K/S, Denmark.

Compositions

The invention also relates to compositions comprising a polypeptide conjugate of the invention.

Said compositions may further comprise polypeptides, such as proteins and/or enzymes and/or ingredients normally used in e.g. detergents, including soap bars, household articles, agrochemicals, personal care products, such as cleaning preparations e.g. for contact lenses, cosmetics, toiletries, oral and dermal pharmaceuticals, composition use for treating textiles, compositions for cleaning hard surfaces, compositions used for manufacturing food, e.g. baking, and feed etc.

Examples of polypeptides being enzymes include proteases, lipases, oxidoreductases, carbohydrases, transferases, such as transglutaminases, anti-microbial polypeptides, and phytases.

Detergent Compositions

Polypeptide conjugates of the invention, such as enzyme conjugates, may typically be a component of a detergent composition, e.g., a laundry detergent composition or a dishwashing detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or non-aqueous.

The detergent composition comprises one or more surfactants, each of which may be anionic, non-ionic, cationic, or amphoteric (zwitterionic). The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of non-ionic surfactant such as alcohol ethoxylate (AEO or AE), alcohol propoxylate, carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more enzymes, such as amylases, pullulanase, esterase, lipase, cutinase, protease, cellulase, peroxidase, or oxidase, e.g., laccase, and anti-microbial polypeptides. One, more or all these polypeptides such as enzymes may be modified (i.e. conjugated) according to the invention.

Normally the detergent contains 1–65% of a detergent builder, but some dishwashing detergents may contain even up to 90% of a detergent builder, or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates as well as layered disilicates and the various types of water-insoluble crystalline or amorphous alumino silicates of which zeolites is the best known representative.

Examples of suitable organic builders include alkali metal, ammonium or substituted ammonium salts of succinates, malonates, fatty acid malonates, fatty acid sulphonates, carboxymethoxy succinates, polyacetates, carboxylates, polycarboxylates, aminopolycarboxylates and polyacetyl carboxylates.

The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, polymaleates, maleic/acrylic acid copolymers and lauryl methacrylate/acrylic acid copolymers.

The detergent composition may contain bleaching agents of the chlorine/bromine-type or the oxygen-type. The bleaching agents may be coated or incapsulated. Examples of inorganic chlorine/bromine-type bleaches are lithium, sodium or calcium hypochlorite or hypobromite as well as chlorinated trisodium phosphate. The bleaching system may also comprise a $H_2O_2$ source such as perborate or percarbonate which may be combined with a peracid-forming bleach activator such as tetraacetylethylenediamine (TAED) or nonanoyloxybenzenesulfonate (NOBS).

Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

In dishwashing detergents the oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED or NOBS.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708. The enzymes of the invention may also be stabilized by adding reversible enzyme inhibitors, e.g., of the protein type as described in EP 0 544 777 B1.

The detergent may also contain other conventional detergent ingredients such as, e.g., fabric conditioners including clays, deflocculant material, foam boosters/foam depressors (in dishwashing detergents foam depressors), suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g. in the range of 7–11.

Particular forms of laundry detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1-2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O,2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes including modified enzymes (calculated as pure enzyme protein) | 0.0001–0.5% |
| Minor inqredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1-2 EO or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O,2SiO_2$) | 1–4% |
| Zeolite (as $NaAlSiO_4$) | 24–34% |
| Sodium sulfate (as $Na_2SO_4$) | 4–10% |
| (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes including modified enzymes (calculated as pure enzyme protein) | 0.0001–0.5% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O,2SiO_2$) | 3–9% |
| Zeolite (as $NaAlSiO_4$) | 23–33% |
| Sodium sulfate (as $Na_2SO_4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes including modified enzymes (calculated as pure enzyme protein) | 0.0001–0.5% |
| Minor ingredients (e.q. suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g. $C_{12-15}$ is alcohol, 7 EO) | 10–25% |
| Sodium carbonate (as $Na_2CO_3$) | 14–22% |
| Soluble silicate (as $Na_2O,2SiO_2$) | 1–5% |
| Zeolite (as $NaAlSiO_4$) | 25–35% |
| Sodium sulfate (as $Na_2SO_4$) | 0–10% |

-continued

| | |
|---|---|
| Carboxymethylcellulose | 0–2% |
| Polymers (e.g. maleic/acrylic acid copolymer, PVP, PEG) | 1–3% |
| Enzymes including modified enzymes (calculated as pure enzyme protein) | 0.0001–0.5% |
| Minor ingredients (e.g. suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes including modified enzymes (calculated as pure enzyme protein) | 0.0001–0.5% |
| Minor ingredients (e.g. dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO, or $C_{12-15}$ alcohol, 5 EO) | 3–9% |
| Soap as fatty acid (e.g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes including modified enzymes (calculated as pure enzyme protein) | 0.0001–0.5% |
| Minor ingredients (e.g. dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O,2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.q. maleic/acrylic acid copolymer, PEG) | 1–5% |
| Enzymes including modified enzymes (calculated as pure enzyme protein) | 0.0001–0.5% |
| Minor ingredients (e.q. optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O,2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes including modified enzymes (calculated as pure enzyme protein) | 0.0001–0.5% |
| Minor ingredients (e.g. suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g. NOBS or TAED) | 1–5% |
| Carboxymethylcellulose | 0–2% |
| Polymers (e.g. polycarboxylate or PEG) | 1–5% |
| Enzymes including modified enzymes calculated as pure enzyme protein) | 0.0001–0.5% |
| Minor ingredients (e.g. optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol, 7 EO, or $C_{12-15}$ alcohol, 5 EO) | 3–9% |
| Soap as fatty acid (e.g. lauric acid) | 0–3% |
| Aminoethanol | 1–5% |

| -continued | |
|---|---|
| Sodium citrate | 5–10% |
| Hydrotrope (e.g. sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes including modified enzymes (calculated as pure enzyme protein) | 0.0001–0.5% |
| Minor ingredients (e.g. polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g. $C_{12-15}$ is alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate/acrylic acid copolymer) | 0–3% |
| Glycerol | 3–8% |
| Enzymes including modified enzymes (calculated as pure enzyme protein) | 0.0001–0.5% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3 \cdot 4H_2O$) | 0–20% |
| Bleach activator (TAED or NOBS) | 0–5% |
| Enzymes including modified enzymes (calculated as pure enzyme protein) | 0.0001–0.5% |
| Minor ingredients (e.g. perfume, optical brighteners) | 0–3% |

13) Detergent formulations as described in 1)–12) wherein all or part of the linear alkylbenzenesulfonate are replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |

| -continued | |
|---|---|
| Zeolite (as $NaAlSiO_4$) | 10–20% |
| Layered disilicate (e.g. SK56 from Hoechst) | 10–20% |
| Sodium carbonate (as $Na_2CO_3$) | 3–12% |
| Soluble silicate (as $Na_2O, 2SiO_2$) | 0–6% |
| Sodium citrate | 4–8% |
| Sodium percarbonate | 13–22% |
| TAED | 3–8% |
| Polymers (e.g. polycarboxylates and PVP) | 0–5% |
| Enzymes including modified enzymes (calculated as pure enzyme protein) | 0.0001–0.5% |
| Minor ingredients (e.g. optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O, 2SiO_2$) | 0–4% |
| Sodium percarbonate | 13–22% |
| TAED | 1–8% |
| carboxymethyl cellulose | 0–3% |
| Polymers (e.g. polycarboxylates and PVP) | 0–3% |
| Enzymes including modified enzymes (calculated as pure enzyme protein) | 0.0001–0.5% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature, 369, (1994), p. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

Particular forms of dishwashing detergent compositions within the scope of the invention include:

| 1) POWDER AUTOMATIC DISHWASHING COMPOSITION | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |

1) POWDER AUTOMATIC DISHWASHING COMPOSITION

| | |
|---|---|
| Sodium perborate | 2–9% |
| Tetraacetylethylenediamine (TAED) | 1–4% |
| Sodium sulphate | 5–33% |
| Enzymes including modified enzymes | 0.0001–0.5% |

2) POWDER AUTOMATIC DISHWASHING COMPOSITION

| | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodiuim perborate monohydrate | 5–10% |
| Tetraacetylethylenediamine (TAED) | 1–2% |
| Polyacrylate polymer (e.g. maleic acid/acrylic acid co-polymer) | 6–25% |
| Enzymes including modified enzymes | 0.0001–0.5% |
| Perfume | 0.1–0.5% |
| Water | 5–10% |

3) POWDER AUTOMATIC DISHWASHING COMPOSITION

| | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetylethylenediamine (TAED) | 0–6% |
| Maleic acid/acrylic acid copolymer | 0–5% |
| Clay | 1–3% |
| Poly(amino acids) | 0–20% |
| Sodium polyacrylate | 0–8% |
| Enzymes including modified enzymes | 0.0001–0.5% |

4) POWDER AUTOMATIC DISHWASHING COMPOSITION

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetylethylenediamine (TAED) | 0–3% |
| Polymer | 0–4% |
| Maleic acid/acrylic acid copolymer | 0–5% |
| Organic phosphonate | 0–4% |
| Clay | 1–2% |
| Enzymes including modified enzymes | 0.0001–0.5% |
| Sodium sulphate | Balance |

5) POWDER AUTOMATIC DISHWASHING COMPOSITION

| | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylenetriaminepentaacetate, pentasodium salt | 0–2.5% |
| Enzymes including modified enzymes | 0.0001–0.5% |
| Sodium sulphate, water | Balance |

6) POWDER AND LIQUID DISHWASHING COMPOSITION WITH CLEANING SURFACTANT SYSTEM

| | |
|---|---|
| Nonionic surfactant | 0–1.5% |
| Octadecyl dimethylamine N-oxide dihydrate | 0–5% |
| 80:20 wt.C18/C16 blend of octadecyl dimethylamine N-oxide dihydrate and hexadecyldimethyl amine N-oxide dihydrate | 0–4% |
| 70:30 wt.C18/C16 blend of octadecyl bis (hydroxyethyl)amine N-oxide anhydrous and hexadecyl bis (hydroxyethyl) amine N-oxide annydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetylethylenediamine (TAED) | 0–4% |
| Maleic acid/acrylic acid copolymer | 0–7.5% |
| Sodium sulphate | 0–12.5% |
| Enzymes including modified enzymes | 0.0001–0.5% |

7) NON-AQUEOUS LIQUID AUTOMATIC DISHWASHING COMPOSITION

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes including modified enzymes | 0.0001–0.5% |

| 8) NON-AQUEOUS LIQUID DISHWASHING COMPOSITION | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes including modified enzymes | 0.0001–0.5% |
| Liquid carrier selected from higher lycols, polyglycols, polyoxides and glycol ethers | Balance |

| 9) THIXOTROPIC LIQUID AUTOMATIC DISHWASHING COMPOSITION | |
|---|---|
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminium tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes including modified enzymes | 0.0001–0.5% |
| Suds suppressor, dye, perfumes, water | Balance |

| 10) LIQUID AUTOMATIC DISHWASHING COMPOSITION | |
|---|---|
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetylethylenediamine (TAFD) | 0–8% |
| Maleic acid/acrylic acid copolymer | 4–8% |
| Enzymes including modified enzymes | 0.0001–0.5% |

| 11) LIQUID AUTOMATIC DISHWASHING COMPOSITION CONTAINING PROTECTED BLEACH PARTICLES | |
|---|---|
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes including modified enzymes | 0.0001–0.5% |
| Water | Balance |

11) Automatic dishwashing compositions as described in 1), 2), 3), 4), 6) and 10), wherein perborate is replaced by percarbonate.

12) Automatic dishwashing compositions as described in 1)–6) which additionally contain a manganese catalyst. The manganese catalyst may, e.g., be one of the compounds described in "Efficient manganese catalysts for low-temperature bleaching", Nature, 369, (1994), p. 637–639.

Personal care applications

Also for personal care products enzyme conjugates with reduced allergenicity of the invention are of interest.

Proteases

Proteases are well-known active ingredients for cleaning of contact lenses. They hydrolyse the proteinaceous soil on the lens and thereby makes it soluble. Removal of thee protein soil is essential for the wearing comfort.

Proteases are also effective ingredients in skin cleaning products, where they remove the upper layer of dead keratinaseous skin cells and thereby make the skin look brighter and more fresh.

Proteases are also used in oral care products, especially for cleaning of dentures, but also in dentifrices.

Further, proteases are used in toiletries, bath and shower products, including shampoos, conditioners, lotions, creams, soap bars, toilet soaps, and liquid soaps.

Lipases

Lipases can be applied for cosmetic use as active ingredients in skin cleaning products and anti-acne products for removal of excessive skin lipids, and in bath and shower products such as creams and lotions as active ingredients for skin care.

Lipases can also be used in hair cleaning products (e.g. shampoos) for effective removal of sebum and other fatty material from the surface of hair.

Lipases are also effective ingredients in products for cleaning of contact lenses, where they remove lipid deposits from the lens surface.

Oxidoreductases

The most common oxidoreductase for personal care purposes is an oxidase (usually glucose oxidase) with substrate (e.g. glucose) that ensures production of $H_2O_2$, which then will initiate the oxidation of for instance $SCN^-$ or $I^-$ into antimicrobial reagents ($SCNO^-$ or $I_2$) by a peroxidase (usually lactoperoxidase). This enzymatic complex is known in nature from e.g. milk and saliva.

It is being utilised commercially as anti-microbial system in oral care products (mouth rinse, dentifrice, chewing gum) where it also can be combined with an amyloglucosidase to produce the glucose. These systems are also known in cosmetic products for preservation.

Anti-microbial systems comprising the combination of an oxidase and a peroxidase are known in the cleaning of contact lenses.

Another application of oxidoreductases are oxidative hair dyeing using oxidases, peroxidases and laccases.

Free radicals formed on the surface of the skin (and hair) known to be associated with the ageing process of the skin (spoilage of the hair).

The free radicals activate chain reactions that leads to destruction of fatty membranes, collagen, and cells. The application of free radical scavengers such as Superoxide dismutase into cosmetics is well-known (R. L. Goldemberg, DCI, Nov. 93, p. 48–52).

Protein disulfide isomerase (PDI) is also an oxidoreductase. It can be utilised for waving of hair (reduction and reoxidation of disulfide bonds in hair) and repair of spoiled hair (where the damage is mainly reduction of existing disulfide bonds).

Carbohydrases

Plaque formed on the surface of teeth is composed mainly of polysaccharides. They stick to the surface of the teeth and the microorganisms. The polysaccharides are mainly $\alpha$-1,6 bound glucose (dextran) and $\alpha$-1,3 bound glucose (mutan). The application of different types of glucanases such as mutanase and dextranase helps hydrolysing the sticky matrix of plaque, making it easier to remove by mechanical action.

Also other kinds of biofilm for instance the biofilm formed in lens cases can be removed by the action of glucanases.

Anti-microbial polypeptides

Anti-microbial polypeptides have widespread applications such as for preservation of cosmetic products, anti-acne products, deodorants and shampoos. Further such polypeptides may be use in contact lens products.

Specific product formulations

Examples of specific personal care compositions can be found in "Cosmetics and Toiletries" edited by Wilfried Umbach and published by Ellis Horwood, Limited, England, (1991), and "Surfactants in Consumer Products", edited by J. Falbe and published by Spring-Verlag, (1987).

In the following a non exhausting list of guide formulations are listed. These provide an overwiev of formulations of important personal care products contemplated according to the invention.

| Ingredients | Examples | % | |
|---|---|---|---|
| Toilet soap | | | |
| Surfactants | Soap (sodium salt) | 83–87 | |
| Sequestering agents | Ethylenediamine tetraacetate | 0.1–0.3 | |
| Consistency regulators | Sodium chloride | approx. 0.5 | |
| Dyestuffs | | <0.1 | |
| Optical brighteners | | <0.1 | |
| Antioxidants | 2,6-bis(1,1-Dimethylethyl) 4-methyl phenol (BHT) | 0.1–0.3 | |
| Whitening agents | Titanium dioxide | 0.1–0.3 | |
| Fragrances | | 1.0–2.0 | |
| Enzymes | Protease/Lipase | 0–5 | |
| Water | | Balance | |
| Syndet (Synthetic Detergents) | | | |
| Surfactants | Lauryl sulfate | 30–50 | |
| | Lauryl sulfo succinate | 1–12 | |
| Refatting agents | Fatty alcohols | 10–20 | |
| Plasticizers | Stearyl mono/diglycerides | 0–10 | |
| Fillers | Starches | 0–10 | |
| Active agents | Salicylic acid | 0–1 | |
| Dyestuffs | | <0.2 | |
| Fragrances | | 0–2 | |
| Enzymes | Protease/Lipase | 0–5 | |
| Water | | Balance | |

| Ingredients | Examples | % Foam bath | % Shower bath |
|---|---|---|---|
| Foam bath and shower bath | | | |
| Surfactants | Lauryl ether sulfate | 10–20 | 10–12 |
| | Coco amidopropyl dimethyl betaine | 2–4 | 2–4 |
| | Ethoxylated fatty acids | 0.5–2 | — |
| Refatting agents | Fatty alcohols | 0.5–3 | |
| | Ethoxylated fatty alcohols | 0.5–5 | 0–4 |
| Enzymes | Protease/Lipase | 0–5 | 0–5 |
| Foam stabilizers | Fatty acid alkanol amides | 0.2–2 | 0–4 |
| Conditioners | Quaternized hydroxypropyl cellulose | — | 0–0.5 |
| Thickeners | Sodium chloride | 0–3 | 0–3 |
| Pearlescent agents | Ethyleneglycol stearate | 0–2 | — |
| Active agents | vegetable extracts | 0–1 | 0–1 |
| Preservatives | 5-Bromo-5-nitro-1,3-dioxane | 0.1 | 0.1 |
| Dyestuffs | | 0.1–0.2 | 0.1 |

-continued

| | | | |
|---|---|---|---|
| Fragrances | | 0.3–3 | 0.3–2 |
| Enzymes | Protease/Lipase | 0–5 | 0–5 |
| Water | | Balance | Balance |

| Ingredients | Examples | % Water-in-oil/ type | Oil-in-water type |
|---|---|---|---|
| Skin cream (water-in-oil type and oil-in-water type) | | | |
| Emulsifiers | Sorbitane sesquioieate | 3–5 | — |
| | Aluminum stearate | 1–2 | — |
| | Triethanolamine stearate | — | 1–2 |
| | Cetyl/Stearyl alcohol polyglycol ethers | — | 1–3 |
| Fatty derivatives | Isopropyl palmitate | 1–5 | 0–3 |
| | Cetyl/Stearyl alcohol | — | 0–2 |
| | 2-octyl dodecanol | 2–10 | 3–7 |
| | Stearic/Palmitic acid | — | 0–3 |
| | Caprylic/Capric acid triglycerides | 5–10 | — |
| | Glycerine stearate | — | 0–5 |
| Moisturizers | Glycerine | 1–5 | 1–5 |
| | Sorbitol | 1–5 | 1–5 |
| | Poly (hydroxy carboxylic acids) | 0.5–2 | — |
| | Propyleneglycol | — | 0–3 |
| Stabilizers | Magnesium sulfate | 0–0.8 | — |
| Preservatives | p-Hydroxy benzoic acid ester | 0.2–0.4 | 0.2–0.4 |
| Enzymes | Protease/Lipase | 0–5 | 0–5 |
| Water | | Balance | Balance |

| Ingredients | Examples | % Body lotion | % Skin lotion |
|---|---|---|---|
| Body lotion (oil-in-water type) and skin lotion for application on the wet skin | | | |
| Emulsifiers | cetyl/stearyl alcohol polyglycol ethers | 1–3 | — |
| | Sorbitane monolaurate | 0.5–1 | — |
| | Sodium stearate | — | 1–2 |
| | Sodium lauryl ether sulfate | — | 0.5–2 |
| Fatty derivatives | 2-octyl dodecanol | 1–3 | 0–5 |
| | Paraflin oils | — | 20–25 |
| | Bees wax | 0.5–1 | — |
| | Isooctyl stearate | 3–7 | — |
| | Isopropyl palmitate | — | 2–5 |
| Moisturizers | Glycerine | 3–5 | 5–10 |
| | Sorbitol | — | 0–5 |
| Thickeners | Polyacrylates | 0–0.3 | 0–1 |
| | Methyl hydroxypropyl cellulose | 0–0.3 | 0–0.5 |
| Preservatives | p-Hydroxy benzoic acid ester | 0.2–0.4 | 0.2–0.4 |
| Enzymes | Protease/Lipase | 0–5 | 0–5 |
| Water | | Balance | Balance |

| Ingredients | Examples | % |
|---|---|---|
| Face lotion | | |
| Surfactants | Magnesium lauryl ether sulfate | 0.2–0.5 |
| Refatting agents | Di-n-butyl adipate | 1–2 |
| Solubilizers | Castor oil polyglycol ethers | 0.1–1 |
| Cleaning and refreshing components | Ethanol | 0–15 |
| Moisturizers | Glycerine | 0–5 |
| | Sorbitol | 0–5 |
| Preservatives | p-Hydroxy benzoic acid | 0.2–0.4 |

| | | -continued |
|---|---|---|
| | ester | |
| Adstringents | vegetable extracts | 1–5 |
| Antiirritants | Panthenol | 0–1 |
| | Allantoine | 0–0.2 |
| | vegetable extracts | 0.5–3 |
| Enzymes | Protease/Lipase | 0–5 |
| Water | | Balance |

Hair shampoo

| | | |
|---|---|---|
| Surfactants | Lauryl ether sulfate | 12–16 |
| | Coco fatty acid amidopropyl dimethyl betaine | 2–5 |
| | Fatty acid polyglycol esters | 0–2 |
| Foam boosters | Fatty acid ethanol amides | 0.5–2.5 |
| Conditioners | Quaternized hydroxyethyl cellulose | 0.4–1 |
| | Protein hydrolysates | 0.2–1 |
| Refatting agents | Ethoxylated lanolin alcohols | 0.2–1 |
| Additives | Anti-dandruff agents | 0–1 |
| Preservatives | 5-Bromo-5-nitro-1,3-dioxane | 0.1–0.3 |
| Pearlescent agents | Ethyleneglycol stearate | 0–2 |
| Dyestuffs | | <0.1 |
| pH-Regulators | Acids/Bases | 0.1–1 |
| Fragrances | | 0.3–0.5 |
| Enzymes | Protease/Lipase | 0–5 |
| Water | | Balance |

| Ingredients | Examples | % Hair rinse | % Hair conditioner |
|---|---|---|---|
| Hair rinse and hair conditioner | | | |
| Surfactants | Fatty alcohol polyglycol ethers | 0.1–0.2 | 1.5–2.5 |
| | Cetyl trimethyl ammonium chloride | 0.5–1 | — |
| | Dimethyl benzyl stearyl ammonium chloride | — | 0.5–.1 |
| Refatting agents | Cetyl/Stearyl mono/diglyceride | 0.5–1.5 | 1.5–2.5 |
| Consistency regulators | Fatty alcohols | 1–2.5 | 2.5–3.5 |
| Thickeners | Methyl hydroxypropyl cellulose | 0.3–0.6 | 0.4–0.8 |
| Conditioners | Quaternized hydroxyethyl cellulose | 0.1–0.3 | 0.3–0.4 |
| Preservatives | p-Hydroxy benzoic acid ester | 0.1–0.3 | 0.1–0.3 |
| Dyestuffs | | <0.1 | <0.1 |
| pH-Regulators | Acids/Bases | 0,1–1 | 0.1–1 |
| Fragrances | | 0.2–0.5 | 0.2–0.5 |
| Enzymes | Protease/Lipase | 0–5 | 0–5 |
| Water | | Balance | Balance |

| Ingredients | Examples | % |
|---|---|---|
| Hair dyes | | |
| Component 1: | Alkaline dyeing cream | |
| Surfactants | Lauryl ether sulfate | 1–4 |
| | Ethoxylated castor oil | 1–2 |
| Consistency regulators | Fatty alcohols | 8–10 |
| Reductants | Sodium sulfite | 0.8–1.2 |
| Buffers | Ammonium chloride | 0.5–1 |
| Sequestrants | 1-Hydroxyethane-1,1-diphosphonic acid | 0.1–0.2 |
| Alkaline agents | Ammonia | 1.2–2 |
| Oxidation dyestuffs | Developing agents | 1 |
| | Coupling agents | 1 |
| Enzyme | Laccase | 0–5 |
| Water | | Balance |
| Component II: | Hydrogen peroxide dispersion | |
| Surfactants | Lauryl ether sulfate | 0.5–1 |
| Oxidants | Hydrogen peroxide | 6–9 |
| Stabilizers | 1-Hydroxyethane-1,1-diphosphonic acid | |

| | -continued | |
|---|---|---|
| Thickeners | Polyacrylates | 3–5 |
| Enzyme | Laccase | 0–5 |
| Water | | Balance |
| Shaving cream | | |
| Soaps | Palmitic/Stearic acid | 30–40 |
| | Potassium hydroxide | 5–7 |
| | Sodium hydroxide | 1–2 |
| Fatty components | Coconut oil | 5–10 |
| | Polyethyleneglycol | 0–2 |
| Stabilizers | Sodium tetraborate | 0–0.5 |
| | Sodium silicate | 0–0.5 |
| | Sorbitol | 0–3 |
| Enzyme | Protease | 0–5 |
| Water | | Balance |
| Shaving lotion | | |
| Disinfecting and phonic acid | Ethanol | 40–80 |
| Refatting agents | Di-n-butyl adipate | 1–2 |
| Solubilizers | Ethoxylated castor oil | 0.5–1 |
| Adstringents | Vegetable extracts | 1–10 |
| Antiirritants | Panthenol | 0–0.5 |
| | Vegetable extracts | 0–2 |
| Stabilizers | Glycerine | 0–5 |
| | Sorbitol | 0–5 |
| | Propyleneglycol | 0–3 |
| Enzymes | Protease | 0–5 |
| Water | | Balance |
| Hair pomade | | |
| Consistency regulators | Fatty alcohols | 4–5 |
| | Ethoxylated lanolin alcohols | 3–6 |
| Mineral fats | Vaseline | 45–52 |
| | Branched chain paraffins | 10–18 |
| Antioxidants | 2,6-bis(1,1-Dimethylethyl)-4-methyl phenol (BHT) | 0.5–1 |
| Fragrances | | 0.2–0.4 |
| Dyestuffs | | 0.1 |
| Enzymes | Lipase | 0–5 |
| Emollients | Glycerine | Balance |
| Setting lotion | | |
| Solvents | Isopropanol | 12–20 |
| Film forming components | Vinyl pyrrolidone/vinyl acetate copolymers | 2–3.5 |
| Softening agents | Vinyl pyrrolidone/dimethyl amino ethyl methacrylate | 0.2–1 |
| Conditioners | Protein hydrolysates | 0.2–0.5 |
| Antistatics | Cetyl trimethyl ammonium chloride | 0.1–0.5 |
| Emulsifiers | Ethoxylated castor oil | 0.1–0.5 |
| Fragrances | | 0.1–0.2 |
| Dyestuffs | | <0.1 |
| Enzymes | Lipase | 0–5 |
| Water | | Balance |

Food and Feed

Further conjugated enzymes or polypeptides with reduced allergenicity according to the invention may advantageously be used in the manufacturing of food and feed.

Proteases

The gluten in wheat flour is the essential ingredient responsible for the ability of flour to be used in baked foodstuffs. Proteolytic enzymes are sometimes needed to modify the gluten phase of the dough, e.g. a hard wheat flour can be softened with a protease.

Neutrase® is a commercially available neutral metallo protease that can be used to ensure a uniform dough quality and bread texture, and to improve flavour. The gluten proteins are degraded either moderately or more extensively to peptides, whereby close control is necessary in order to avoid excessive softening of the dough.

Proteases are also used for modifying milk protein.

To coagulate casein in milk when producing cheese proteases such as rennet or chymosin may be used.

In the brewery industry proteases are used for brewing with unmalted cereals and for controlling the nitrogen content.

In animal feed products proteases are used so to speak to expand the animals digestion system.

Lipases

The application of lipase in the baking industry is rather new. Addition of lipase results in improved dough properties and an improved breadmaking quality in terms of larger volume, improved crumb structure and whiter crumb colour. The observed effect can be explained by a mechanism where the Lipase changes the interaction between gluten and some lipids fragment during dough mixing. This results in an improved gluten network.

The flavour development of blue roan cheeses (e.g. Danablue), certain Italian cheese types and other dairy products containing butter fat are dependent on the degradation of milk fat into free fatty acids. Lipases may be used for developing flavour in such products.

In the oil- and fat producing industry lipases are used e.g. to minimize the amount of undesirable side-products, to modify fats by interesterification, and to synthesis of esters.

Oxidoreductases

Further oxidoreductases with reduced allergenicity according to the invention may advantageously be used in the manufacturing of food and feed.

Several oxidoreductases are used for baking, glucose oxidase, lipoxygenase, peroxidase, catalase and combinations hereof. Traditionally, bakers strengthen gluten by adding ascorbic acid and potassium bromate. Some oxidoreductases can be used to replace bromate in dough systems by oxidation of free sulfydryl units in gluten proteins. Hereby disulphide linkages are formed resulting in stronger, more elastic doughs with greater resistance.

Gluzyme™ (Novo Nordisk A/S) is a glucose oxidase preparation with catalase activity that can be used to replace bromate. The dough strengthen is measured as greater resistance to mechanical shock, better oven sp ring and larger loaf volume.

Carbohydrases

Flour has varying content of amylases leading to differences in the baking quality. Addition of amylases can be necessary in order to standardize the flour. Amylases and pentosanases generally provide sugar for the yeast fermentation, improve the bread volume, retard retrogradation, and decrease the staling rate and stickiness that results from pentosan gums. Examples of carbohydrases are given below.

Certain maltogenic amylases can be used for prolonging the shelf life of bread for two or more days without causing gumminess in the product. Selectively modifies the gelatinized starch by cleaving from the non-reducing end of the starch molecules low molecular wight sugars and dextrins. The starch is modified in such a way that retrogradation is less likely to occur. The produced low-molecular-weight sugars improve the baked goods water retention capacity without creating the intermediate-length dextrins that result in gumminess in the finished product. The enzyme is inactivated during bread baking, so it can be considered a processing aid which does not have to be declared on the label. The overdosing of Novamyl can almost be excluded.

The bread volume can be improved by fungal α-amylases which further provide good and uniform structure of the bread crumb. Said α-amylases are endoenzymes that produce maltose, dextrins and glucose. Cereal and some bacterial α-amylases are inactivated at temperatures above the gelatinization temperature of starch, therefore when added to a wheat dough it results in a low bread volume and a sticky bread interior. Fungamyl has the advantage of being thermolabile and is inactivated just below the gelatinization temperature.

Enzyme preparations containing a number of pentosanase and hemi-cellulase activities can improve the handling and stability of the dough, and improves the freshness, the crumb structure and the volume of the bread.

By hydrolysing the pentosans fraction in flour, it will lose a great deal of its water-binding capacity, and the water will then be available for starch and gluten. The gluten becomes more pliable and extensible, and the starch gelatinize more easily. Pentosanases can be used in combination with or as an alternative to emulsifiers.

Further carbohydrases are user for producing syrups from starch, which are widely used in soft drinks, sweets, meat products, dairy products, bread products, ice cream, baby food, jam etc.

The conversion of starch is normally carried out in three steps. First the starch is liquefied, by the use of α-amylases. Maltodextrins, primary consisting of oligosaccharides and dextrins, are obtained.

The mixture is then treated with an amyloglucosidase for hydrolysing the oligosaccharides and dextrins into glucose. This way a sweeter product is obtained. If high maltose syrups are desired β-amylases alone or in combination with a pullulanase (de-branching enzyme) may be used.

The glucose mixture can be made even sweeter by isomerization to fructose. For this an immobilized glucose isomerase can be used.

In the sugar industry, it is common practice to speed up the break down of present starch in cane juices. Thereby the starch content in the raw sugar is reduced and filtration at the refinery is facilitated.

Furthermore dextranases are used to break down dextran in raw sugar juices and syrups.

In the alcohol industry α-amylases are advantageously being used for thinning of starch in distilling mashes.

In the brewing industry α-amylases are used for adjunct liquefaction.

In the dairy industry β-galactosidases (lactase) are used when producing low lactose milk for persons suffering from lactose malabsorption.

When flavoured milk drinks are produced from lactase-treated milk, the addition of sugar can be reduced without reducing the sweetness of the product.

In the production of condensed milk, lactose crystallization can be avoided by lactase treatment, and the risk of thickening caused by casein coagulation in lactose crystals is thus reduced.

When producing ice cream made from lactase-treated milk (or whey) no lactose crystals will be formed and the defect, sandiness, will not occur.

Further, xylanases are known to be used within a number of food/feed industrial applications as described in WO 94/21785 (Novo Nordisk A/S).

α-amylases are used in the animal feed industry to be added to cereal-containing feed to improve the digestibility of starch.

Anti-microbial polypeptides

Certain bacteriolytic enzymes may be used e.g. to wash carcasses in the meat packing industry (see U.S. Pat. No. 5,354,681 from Novo Industri A/S)

Transferases

Transglutaminases with reduced allergenicity according to the invention may advantageously be used in the manufacturing of food and feed.

Transglutaminases have the ability to crosslinking protein.

This property can be used for gelling of aqueous phases containing proteins. This may be used for producing spreads (DK patent application no. 1071/84 from Novo Nordisk A/S).

Transglutaminases are being used for improvement of baking quality of flour e.g. by modifying wheat flour to be used in the preparation of cakes with improved properties, such as improved taste, dent, mouth-feel and a higher volume (see JP 1-110147).

Further producing paste type food material e.g. used as fat substitution in foods as ice cream, toppings, frozen desserts, mayonnaise and low fat spreads (see WO 93/22930 from Novo Nordisk A/S).

Furthermore for preparation of gels for yoghurt, mousses, cheese, puddings, orange juice, from milk and milk-like products, and binding of chopped meat product, improvement of taste and texture of food proteins (see WO 94/21120 and WO 94/21129 from Novo Nordisk A/S).

Phytases

Phytases of the invention may advantageously be used in the manufacturing of food, such as breakfast cereal, cake, sweets, drink, bread or soup etc., and animal feed.

Phytases may be used either for exploiting the phosphorus bound in the phytate/phytic acid present in vegetable protein sources or for exploiting the nutritionally important minerals bound in phytic acid complexes.

Microbial phytase may be added to feedstuff of monogastric animals in order to avoid supplementing the feed with inorganic phosphorus (see U.S. Pat. No. 3,297,548)

Further phytases may be used in soy processing. Soy bean meal may contain high levels of the anti-nutritional factor phytate which renders this protein source unsuitable for application in baby food and feed for fish, calves and other non-ruminants, since the phytate chelates essential minerals present therein (see EP 0 420 358).

Also for baking purposes phytases may be used. Bread with better quality can be prepared by baking divided pieces of a dough containing wheat flour etc. and phytase (see JP-0-3076529-A)

A high phytase activity koji mold are known to be used for producing refined sake (see JP-0-6070749-A).

Textile applications

Proteases

Proteases are used for degumming and sand-washing of silk.

Lipases

Lipases are used for removing fatty matter containing hydrophobic esters (e.g. triglycerides) during the finishing of textiles (see e.g. WO 93/13256 from Novo Nordisk A/S).

Oxidoreductases

In bleach clean-up of textiles catalases may serve to remove excess hydrogen peroxide.

Carbohydrases

Cellulolytic enzymes are widely used in the finishing of denim garments in order to provide a localized variation in the colour density of the fabric (Enzyme facilitated "stone wash").

Also cellulolytic enzymes find use in the bio-polishing process. Bio-Polishing is a specific treatment of the yarn surface which improves fabric quality with respect to handle and appearance without loss of fabric wettability. Bio-polishing may be obtained by applying the method described e.g. in WO 93/20278.

During the weaving of textiles, the threads are exposed to considerable mechanical strain. In order to prevent breaking, they are usually reinforced by coating (sizing) with a gelatinous substance (size). The most common sizing agent is starch in native or modified form. A uniform and durable finishing can thus be obtained only after removal of the size from the fabric, the so called desizing. Desizing of fabrics sized with a size containing starch or modified starch is preferably facilitated by use of amylolytic enzymes.

Oral and dermal pharmaceuticals

Proteases

Different combinations of highly purified proteases (e.g. Trypsin and Chymotrypsin) are used in pharmaceuticals to be taken orally, and dermal pharmaceuticals for combating e.g. inflammations, edemata and injuries.

Leather production

Transferase

Transglutaminase is known to be used for casein finishing of leather by acting as a hardening agent (see WO 94/13839 from Novo Nordisk).

Hard surface cleaning

Cleaning of hard surfaces e.g. in the food industry is often difficult, as equipment used for producing dairies, meat, sea food products, beverages etc. often have a complicated shape. The use of surfactant compositions in the form gels and foams comprising enzymes have shown to facilitate and improve hard surface cleaning. Enzymes, which advantageously may be added in such surfactant compositions, are in particular proteases, lipases, amylases and cellulases.

Such hard surface cleaning compositions comprising enzymes may also advantageously be used in the transport sector, for instance for washing cars and for general vessel wash.

Finally the invention relates to the use of the conjugate of the invention or a composition of the invention in products comprising polypeptides.

First of all the conjugate or compositions of the invention can advantageously be used for personal care products, such as hair care and hair treatment products. This include products such as shampoo, balsam, hair conditioners, hair waving compositions, hair dyeing compositions, hair tonic, hair liquid, hair cream, shampoo, hair rinse, hair spray.

Further contemplated is oral care products such as dentifrice, mouth washes, chewing gum.

Also contemplated are skin care products and cosmetics, such as skin cream, skin milk, cleansing cream, cleansing lotion, cleansing milk, cold cream, cream soap, nourishing essence, skin lotion, milky lotion, calamine lotion, hand cream, powder soap, transparent soap, sun oil, sun screen, shaving foam, shaving cream, baby oil lipstick, lip cream, creamy foundation, face powder, powder eye-shadow, powder, foundation, make-up base, essence powder, whitening powder.

Also for contact lenses hygiene products the conjugate of the invention can be used advantageously. Such products include contact lenses cleaning and disinfection products.

The use for detergents such as washing powder, soap, soap bars, liquid soap are also contemplated.

Materials and Method

Enzymes:

Monomer purified peroxidase ($M_r$=39 kDa) derived from wild-type *Coprinus cinereus* (available from Novo Nordisk A/S).

Lipase: Lipolase® (from Novo Nordisk A/S)

Cellulase: Carezyme® core prepared as described according to Boisset, C. et al. (1995), FEBS Lett. 376, p. 49–52.

Dextran-peroxidase A (prepared by Kem-En-Tech, Denmark).

Dextran-peroxidase B (prepared by Kem-En-Tech, Denmark).

Dextran-cellulase (prepared by Kem-En-Tech, Denmark).

Dextran-lipase (prepared by Kem-En-Tech, Denmark).

Solutions

PBS Tween20 Ausubel, F. M. et al. (Editors), 1994

Rabbit anti-goat (Sigma A-4187)

Alkaline phosphatase Buffer (pH=9.0)

NaCl 5.844 g

MgCl$_2$,6H$_2$O 1.02 g
Diethanol amine 10.51 g
The pH is adjusted to 9.0 with HCl, and Milli-Q water is applied to 1 liter.

| Stop-solution | |
| --- | --- |
| EDTA, disodium | 74.44 g |
| K$_2$HPO$_4$ | 174.2 g |
| NAH$_3$ | 0.2 g |

The pH is adjusted to 10 with about 22.5 g KOH in Milli-Q water to 1 litre.

Test animals

Dunkin Hartley guinea pigs (from Charles River, Del.)

Equipment

ELISA reader: Ceres 900 HDi

Preparation of anti-lipase and anti-cellulase, anti-peroxidase

White New Zealand rabbits are used. 2–4 rabbits per antigen.

FCI(Freund incomplete adjuvant) is used.

50–100 μg enzyme protein is used per rabbit per injection.

For mono-specific antibody production very high purified antigen is used.

Each rabbit is given an injection in the back of the neck (subcutaneous) with 1 ml fresh stable mix of 1:1 antigen and adjuvant.

Injection weekly up till 10 weeks.

1 blood sample from the rabbit is taken after the fifth immunization and checked in Ouchtterrlony (Nils H Axelsen, (1983), "Handbook of Immunuprecipitation-in-Gel Techniques", Blackwell Scientific Publication) when the titer shows ⅟₁₈–⅟₃₂ blood is drawn from the rabbits and antibodies are purified.

ELISA procedure for determination of IqG$_1$ positive guinea pigs

ELISA microtiter plates are coated with rabbit anti-peroxidase 1:8000, rabbit anti-cellulase 1:8000 and anti-lipase 1:6000, respectively, in carbonate buffer and incubated over night at 4° C. The next day the plates are blocked with 2% BSA for 1 hour and washed 3 times with PBS tween 20.

Peroxidase, cellulase Core and lipase were added to the relevant plates. 1 μg enzyme protein/ml.

All guinea pig sera samples are applied to the ELISA plates with 10 μl sera and 90 μl PBS for peroxidase, and 1:50 dilutions of sera for cellulase and lipase, incubated for 1 hour and washed 3 times with PBS Tween20.

Then goat anti-guinea pig IgG$_1$ and 0.5% BSA 1:4000 in PBS buffer (Nordic Immunology 44–682) is applied to the plates, incubated for 1 hour and washed with PBS Tween20.

Alkaline phosphatase marked rabbit anti-goat 1:8000 is applied and incubated for 1 hour, washed 2 times in PBS Tween20 and 1 time with diethanol amine buffer.

The marked alkaline phophatase is developed using p-nitrophenyl phosphate for 30 minutes at 37° C. and stopped with calcium/sodium buffer comprising EDTA (pH 10) and read at OD 405/650 using a ELISA reader.

Double blinds are included on all ELISA plates.

Positive and negative sera values are calculated as the average blind values added 2 times the standard deviation. This gives an accuracy of 95%.

The test is described more thoroughly in APR 95255001, ED-9516670 available on request from Novo Nordisk A/S.

EXAMPLES

Example 1

Allergenicity trails with modified peroxidase

Dunkin Hartley guinea pigs were exposed to 1.0 μg purified monomer *Coprinus cinerea* peroxidase (guinea pig 21–30) and 1.0 μg modified dextran-peroxidase A (guinea pig 31–40) and dextranperoxidase B (guinea pig 41–50) by intratracheal dosage as described ED-9516670 available on request from Novo Nordisk A/S.

All guinea pigs were tested for the production of IgG$_1$ (indicating an allergic response) during 8 weeks using the ELISA procedure described above.

Figure 1:
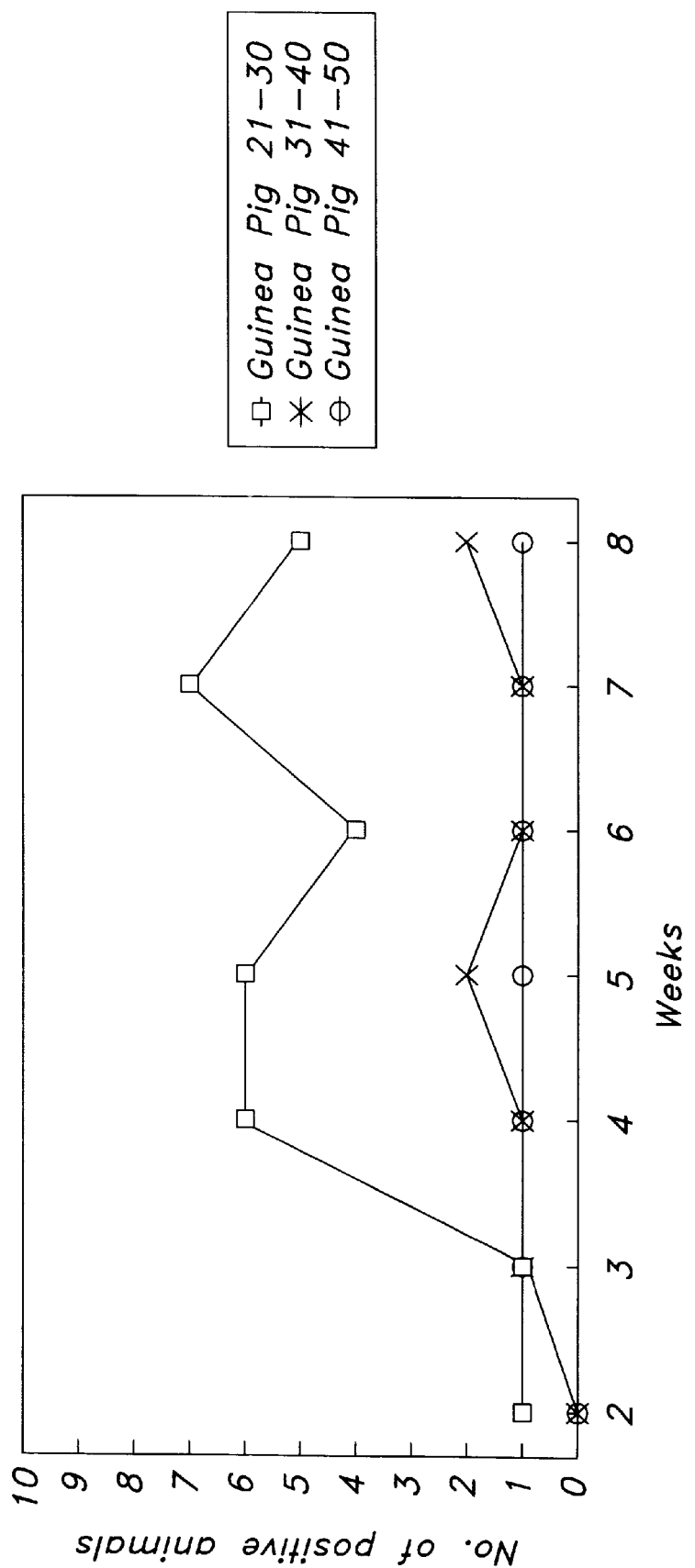
FIG. 1 shows the number of Dunkin Hartley guinea pig having been exposed to 1.0 μg monomer Peroxidase and 1.0

FIG. 1 shows the number of Dunkin Hartley guinea pigs found IgG$_1$ positive during the trail period.

It can be seen from FIG. 1 the number of guinea pigs being IgG$_1$ positive at any time during the trial period is reduced for both dextran-peroxidase A and B in comparison to the monomer peroxidase. This proves that the allergenicity of polypeptides can be reduced by coupling to a suitable polymeric carrier molecule such as dextran.

Example 2

Allergenicity trails with modified lipase

The trails described in Example 1 were repeated, except that the Dunkin Hartley guinea pigs were stimulated intratracheally with either 1 μg purified lipase or 1 μg purified modified lipase.

All guinea pigs were tested for the production of IgG$_1$ (indicating an allergic response) during 10 weeks using the ELISA procedure described above.

As can be seen from FIG. 2 the modified lipase has a reduced allergenicity.

Example 3

Allergenicity trails with modified cellulase

The trails described in Example 1 were repeated, except that the Dunkin Hartley guinea pigs were stimulated intratracheally with either 1 μg purified cellulase or 1 μg purified modified cellulase.

All guinea pigs were tested for the production of, IgG$_1$ (indicating an allergic response) during 10 weeks using the ELISA procedure described above.

As can be seen from FIG. 3 the modified lipase has a reduced allergenicity. As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An isolated polypeptide conjugate with reduced respiratory allergenicity comprising a polymeric carrier molecule having two or more polypeptide molecules coupled thereto.

2. The conjugate according to claim 1 wherein the polypeptide molecules are coupled directly to the polymeric carrier molecule.

3. The conjugate according to claim 2 wherein the polypeptide molecules are coupled to the polymeric carrier molecule via a linker molecule.

4. The conjugate according to claim 3 wherein the polymeric carrier molecule is coupled to the polypeptide molecules via a divinyl sulfone, the coupling being a covalent linkage formed between one of the two vinyl groups of the divinl sulfone.

5. The conjugate according to claim 1, wherein the polymeric carrier molecule is selected from the group consisting of natural and synthetic homo- and heteropolymers.

6. The conjugate according to claim 5, wherein the polymeric carrier molecule is a synthetic polymeric molecule selected from the group consisting of Star-polyethylene glycols (PEGs), Branched PEGs, polyvinyl alcohol (PVA), polycarboxyl acids, polyvinylpyrrolidone and poly-D,L-amino acids.

7. The conjugate according to claim 5, wherein the polymeric carrier molecule is a natural occurring polymeric molecule selected from the group consisting of dextrans, celluloses, hydrolysates of chitosan, starches, glycogen, agarose, guar gum, inulin, pullulan, xanthan gums carrageenin, pectin and alginic acid.

8. The conjugate according to claim 1, wherein the polypeptide is a protein of plant, animal or microbial origin.

9. The conjugate according to claim 1, wherein the polypeptide is an anti-microbial polypeptide.

10. The conjugate according to claim 8, wherein the polypeptide is an enzyme.

11. The conjugate according to claim 10, wherein the enzyme is a protease, a lipase, a transferase, a carbohydrase, an oxidoreductase, or a phytase.

12. The conjugate according to claim 10, wherein the enzyme has a molecular weight ($M_r$) of from about 4 kDa to 200 kDa.

13. The conjugate according to claim 1, wherein the molecular weight of the polymeric carrier molecule lies between 1 kDa and 10,000 kDa.

14. The conjugate according to claim 1, wherein the total molecular weight ($M_r$) of the conjugated molecule lies between 50 kDa and 40,000 kDa.

15. The conjugate according to claim 1, wherein between 2 and 60 polypeptide molecules are coupled to one polymeric carrier.

16. The conjugate according to claim 1, wherein two or more different polypeptide molecules are coupled to each polymeric carrier molecule.

17. The conjugate according to claim 16, comprising one or more enzyme molecules and one or more ligand molecules.

18. The conjugate according to claim 16, comprising one or more antibody molecules and one or more inhibitor molecules.

19. The conjugate according to claim 16, comprising one or more receptor molecules and one or more antibody molecules.

20. A process of producing polypeptide molecules with reduced allergenicity comprising the steps of
   i) activating a polymeric carrier molecule, and
   ii) reacting one or more polypeptide molecules with said activated polymeric carrier molecule under conditions suitable for conjugation, and
   iii) blocking of residual active groups on the conjugate.

21. The process according to claim 20, comprising the steps of
   a) activating a polymeric carrier molecule by coupling thereto a reactive moiety, and
   b) reacting two or more polypeptide molecules with said activated polymeric carrier molecule.

22. The process according to claim 21 wherein the activation of the polymeric carrier molecule in step a) is performed by covalently linking thereto a reactive moiety derived from divinylsulfone.

23. The process according to claim 20, wherein the polymeric carrier molecule is selected from the group consisting of natural and synthetic homo- and heteropolymers.

24. The process according to claim 20, wherein the polypeptide molecules of plant, animal, or microbial origin.

25. The process according to claim 20, wherein the polymeric carrier molecule is coupled with the polypeptide molecules via an amino group (—$NH_2$), a hydroxy group (—OH), a carboxylic acid group (—COOH) or a thiol group on the polypeptide molecules.

26. A composition comprising a conjugate according to claim 1.

27. The composition according to claim 26, wherein the composition further comprises at least one of polypeptides, proteins enzymes and ingredients normally used in detergents, household articles, agrochemicals, personal care products, cosmetics, toiletries, pharmaceuticals, compositions for treating textiles, compositions for cleaning hard surfaces, or compositions used for manufacturing food and feed.

28. The conjugate according to claim 7, wherein the dextrans include carboxymethyl dextrans.

29. The conjugate according to claim 7, wherein the celluloses include methylcellulose, carboxymethylcellulose, ethylcellulose, hydroxyethylcellulose, hydroxypropylcellulose.

30. The conjugate according to claim 7, wherein the starches include hydroxyethyl-starches and hydroxypropyl-starches.

31. The conjugate according to claim 12, wherein the molecular weight is from about 15 kDa to 150 kDa.

32. The conjugate according to claim 31, wherein the molecular weight is from about 20 to 100 kDa.

33. The conjugate according to claim 13, wherein the molecular lies between 2 kDa and 5,000 kDa.

34. The conjugate according to claim 33, wherein the molecular weight lies between 5 kDa and 500 kDa.

35. The conjugate according to claim 14, wherein the total molecular weight of the conjugated molecule lies between 100 kDa and 1,000.

36. The conjugate according to claim 35, wherein the total molecular weight of the conjugated molecule lies between 200 kDa and 500 kDa.

37. The conjugate according to claim 15, wherein 2 and 40 polypeptide molecules are coupled to one polymeric carrier.

38. The conjugate according to claim 37, wherein 3 and 20 polypeptide molecules are coupled to one polymeric carrier.

39. The composition of claim 26 which is a detergent.

40. The composition of claim 26 which is a personal care product.

* * * * *